United States Patent [19]

Aarts

[11] Patent Number: 5,103,003
[45] Date of Patent: Apr. 7, 1992

[54] 3-(1,3-OXAZOLIDINYL)-S-TRIAZINE

[75] Inventor: Veronika M. L. J. Aarts, Beek, Netherlands

[73] Assignee: Stamicarbon B.V., Geleen, Netherlands

[21] Appl. No.: 501,038

[22] Filed: Mar. 29, 1990

[30] Foreign Application Priority Data

Mar. 30, 1989 [NL] Netherlands .......................... 8900777

[51] Int. Cl.⁵ ............................................. C07D 251/70
[52] U.S. Cl. ..................................................... 544/198
[58] Field of Search .......................................... 544/198

[56] References Cited
PUBLICATIONS

Dovlatyan et al., Chemical Abstracts, vol. 99, entry 139913 (n) 1983.

Primary Examiner—John M. Ford
Attorney, Agent, or Firm—Cushman, Darby & Cushman

[57] ABSTRACT

The invention relates to 3-(1,3-oxazolidinyl)-s-triazine and the preparation thereof by the reaction of the corresponding N-(2-hydroxethyl)melamine with formaldehyde. Di- and tri-3-(1,3-oxazolidinyl)-s-triazine in particular can be used with advantage as cross-linking agents in polymerization reactions in which no volatile reaction products may be formed.

5 Claims, No Drawings

3-(1,3-OXAZOLIDINYL)-S-TRIAZINE

The invention relates to 3-(1,3-oxazolidinyl)-s-triazine and the preparation thereof.

3-(1,3-oxazolidinyl)-s-triazine is represented by the following formula (1)

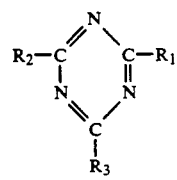

where:

$R_1$ is 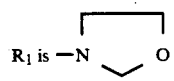

$R_2$ and $R_3$ are $-NH_2$, 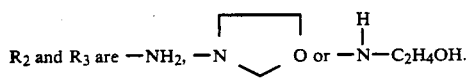

The oxazolidinyl group of these compounds shows great reactivity. For this reason 2-amino-4,6-di-3-(1,3-oxazolidinyl)-s-triazine and 2,4,6-tri-3-(1,3-oxazolidinyl)-s-triazine in particular are suitable for use as cross-linking agents in polymerisation reactions.

The 3-(1,3-oxazolidinyl)-s-triazine according to the invention presents particular advantages compared with hexamethoxymethyl melamine, which is currently being used on a large scale and which, in functional terms, contains at least 3 formaldehyde groups too many and may therefore give rise to environmental problems by formaldehyde emission when processed.

Polymerisation reactions in which di- and trioxazolidinyltriazines according to the invention may be used as cross-linking agents are particularly reactions in which no volatile compounds, such as formaldehyde, may be formed and/or applications in which the cross-linking agent is mixed in as a solid.

The oxazolidinyltriazines according to the invention can be obtained in a simple manner with a surprisingly high yield and purity by reacting the corresponding 2-hydroxyethyl melamine compounds (2) with formaldehyde

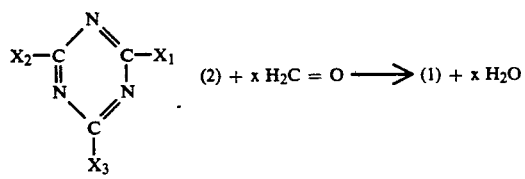

where:

$X_1 = X_2 = X_3 = $ 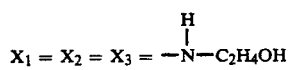

(N,N',N''-tris(2-hydroxyethyl)melamine), or $X_1 = X_2 = $ 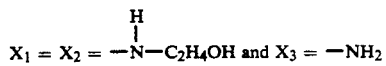 and $X_3 = -NH_2$ (N,N'-bis(2-hydroxyethyl)melamine), or $X_1 = $ 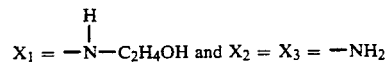 and $X_2 = X_3 = -NH_2$ (N,(2-hydroxyethyl)melamine), or mixtures of two or more of these compounds.

The reaction is preferably carried out at an elevated temperature, of for instance 40°-100° C., in an aqueous medium. The oxazolidinyl triazine formed precipitates from the reaction mixture as the reaction progresses and a high yield of a high purity can be obtained with the usual means, for example filtration. Depending on the type of 2-hydroxyethyl melamine chosen as starting material and the amount of formaldehyde used a wide range of oxazolidinyltriazines is obtained.

In a typical embodiment the hydroxyethyl melamine is dissolved in an approximately 30 wt. % formaldehyde solution in water, which is then heated to abt. 80° C. After 30 minutes the oxazolidinyl triazine formed in the reaction starts to precipitate. This is removed by filtration after cooling. Depending on the chosen starting materials and the amount of formaldehyde used, the individual compounds or mixtures thereof are obtained.

2-Hydroxyethyl melamine compounds can be obtained with the aid of various processes already known per se. Examples of these are: the reaction of ethanolamine with a melamine, substituted if so desired, at a temperature between 100° and 250° C., in the presence of an acid catalyst, as described in U.S. Pat. No. 4,312,988 and EP-B-160.297, or the reaction of cyanuric chloride with ethanolamine at a temperature of 0°-100° C. in the presence of NaOH in dioxane/cellosolve, as described in J. Am. Chem. Soc. 73, 2981-2986 (1951).

Surprisingly, the simple synthesis route according to the invention results in oxazolidinyl triazine which is not contaminated by resins and the like, as would be expected on the basis of the great reactivity of formaldehyde and melamine.

The invention will now be further elucidated with the following examples and comparative example without, however, being limited thereto.

EXAMPLE I

N,N',N''-tris(2-hydroxyethyl)melamine (produced from melamine according to the process of EP-B-166297) (4.9 g, 19 mmoles) was dissolved in 5.7 g of a 30% formaldehyde solution. After 30 minutes' stirring at 90° C. the reaction mixture was cooled to room temperature. The precipitated reaction product was removed by filtration, dried (1.4 g, melting point 179°-180° C.) and characterized with the aid of NMR (400 MHz); 83% of the hydroxyethyl groups originally present had been converted into oxazolidine rings, the residual 17% still being present in the form of free hydroxyethyl groups.

EXAMPLE II

N,N',N'''-tris(2-hydroxyethyl)melamine (produced from cyanuric chloride) (0.5 g, 1.9 mmoles) was dissolved in 2.5 mL of water and 1.2 g of 30% formaldehyde solution. After 1 hour's refluxing the reaction mixture was cooled to room temperature and the precipitated reaction product was filtered off and dried. The product with a melting range of 190°–210° C. was characterized with the aid of NMR as indicated in example I; 95% of the hydroxyethyl groups originally present had been converted into oxazolidine rings, the residual 5% still being present in the form of free hydroxyethyl groups.

COMPARATIVE EXAMPLE A 2 g of a mixture of mono, N,N'-bis and N,N',N''-tris(-hydroxyisopropyl)melamine (7:51:41) was dissolved in 5 g of water and 1.8 g of a 30% formaldehyde solution. After 2 hours' refluxing the reaction mixture was cooled to room temperature and evaporated with a rotary film evaporator. The residual product with a melting range of 255°–270° C. was characterized with NMR; only 10% of the hydroxyisopropyl groups had been converted into oxazolidine rings.

I claim:

1. 3-(1,3-oxazolidinyl)-s-triazine of the formula (1)

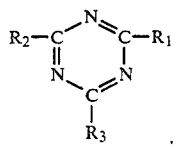

where:

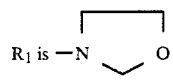

and

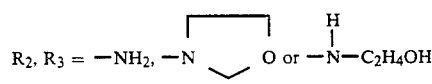

2. 3-(1,3-oxazolidinyl)-s-triazine according to claim 1, characterized in that

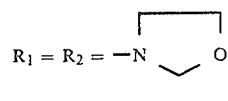

and

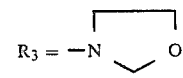

or

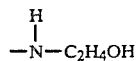

3. 3-(1,3-oxazolidinyl)-s-triazine according to claim 2, characterized in that

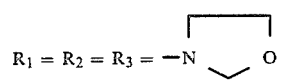

4. A process for the preparation of a 3-(1,3-oxazolidinyl)-s-triazine, as claimed in claim 1, comprising the reaction of a compound of formula II:

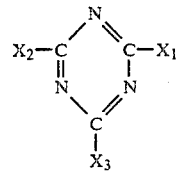

wherein $X_1$ is —$NHC_2H_4OH$, and
$X_2$ and $X_3$ are each independently selected from —$NH_2$ and $NHC_2H_4OH$; with formaldehyde at an elevated temperature.

5. Process according to claim 4, characterized in that the reaction is carried out in an aqueous medium at a temperature between 40° and 100° C.

* * * * *

UNITED STATES PATENT AND TRADEMARK OFFICE
CERTIFICATE OF CORRECTION

PATENT NO. : 5,103,003
DATED      : April 7, 1992
INVENTOR(S) : Aarts

It is certified that error appears in the above-identified patent and that said Letters Patent is hereby corrected as shown below:

In Column 2, line 36, change "EP-B-160.297" to --EP-B-166.297--.

Signed and Sealed this

Seventh Day of September, 1993

Attest:

BRUCE LEHMAN

*Attesting Officer*    *Commissioner of Patents and Trademarks*